United States Patent [19]

Tsay et al.

[11] Patent Number: 5,561,108
[45] Date of Patent: Oct. 1, 1996

[54] PREPARATION OF $\alpha_1$-ANTICHYMOTRYPSIN

[75] Inventors: Grace C. Tsay, Walnut Creek; Neal K. H. Cheung, Vallejo; Jeffrey D. Bettencourt, Walnut Creek, all of Calif.

[73] Assignee: Bayer Corporation, Elkhart, Ind.

[21] Appl. No.: 282,860

[22] Filed: Jul. 29, 1994

[51] Int. Cl.$^6$ .............. C07K 1/18; C07K 1/22; C07K 14/47; A61K 38/17
[52] U.S. Cl. .......... 514/12; 530/380; 530/395; 530/415; 530/416; 530/830
[58] Field of Search .............. 530/380, 395, 530/412, 415, 416, 829, 830, 831; 514/12; 435/183

[56] References Cited

U.S. PATENT DOCUMENTS 4,379,087  4/1983  Coan et al. .............. 530/380
5,079,336  1/1992  Rubin et al. .............. 530/350

OTHER PUBLICATIONS

Travis et al. Biochemistry 17(26) 5647–5651 1978.
Laine et al. Biochim Biophys Acta 668 429–438 1981.
Laine et al. Eur. J. Biochem 197 209–215 1991.
Laine et al Clin Chim Acta 190 163–174 1990.
Abdullah et al. Arch Biochem Biophys. 225(1) 306–312 1983.
Siddiqui et al Biochem Biophys Res. Commun. 95(4) 1737–1742 1980.

*Primary Examiner*—Mindy Fleisher
*Assistant Examiner*—Nancy J. Degen
*Attorney, Agent, or Firm*—James A. Giblin

[57] ABSTRACT

Human $\alpha_1$-antichymotrypsin (ACT) can be purified from solutions containing human $\alpha_1$-proteinase inhibitor (PI) and antithrombin III (AT-III) using chromatography adsorption steps at carefully controlled pH and conductivity. The separated ACT retains in vitro inhibitory capacity and has potential therapeutic use.

1 Claim, 2 Drawing Sheets

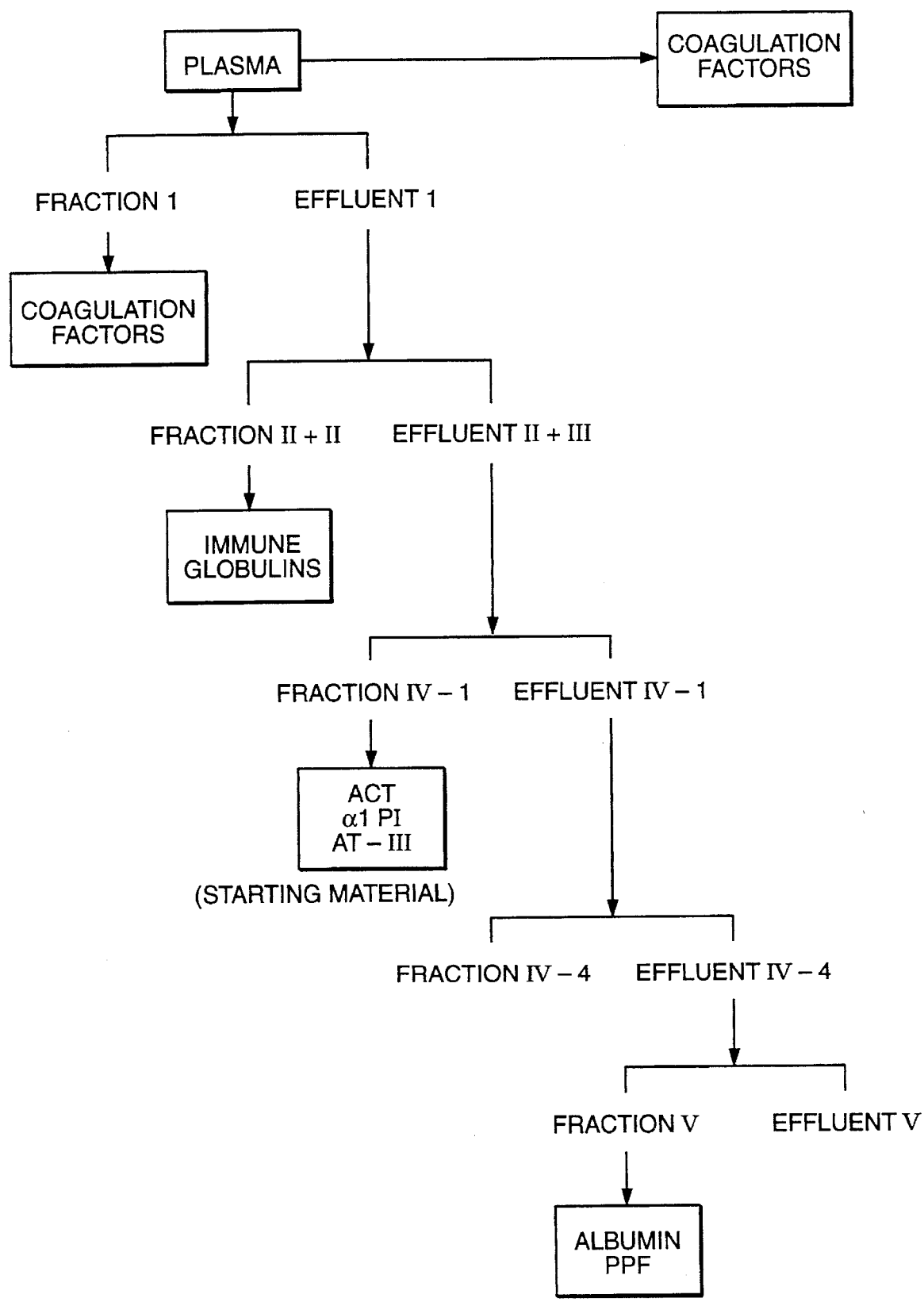
FIG._1

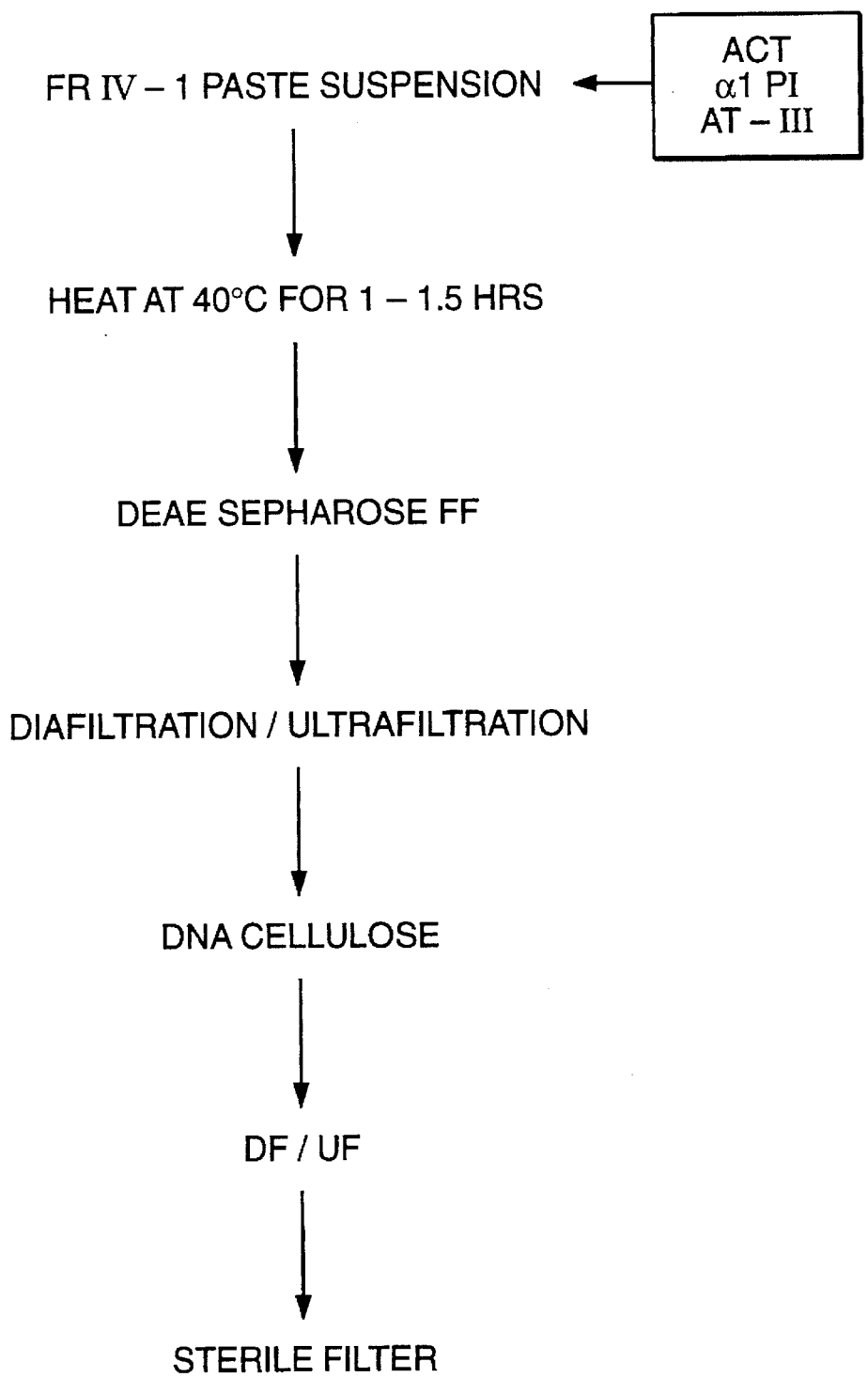
FIG._2

PREPARATION OF α₁-ANTICHYMOTRYPSIN

BACKGROUND OF THE INVENTION

1. Field

This disclosure relates generally to the preparation of human blood plasma proteins and specifically with the preparation of alpha$_1$-antichymotrypsin (ACT) from a mixture of ACT, alpha$_1$-proteinase inhibitor (PI) and antithrombin III (AT-III) such as that found in Cohn Fraction IV-1 paste suspension obtained from human plasma.

2. Prior Art

Before the Second World War, scientists and physicians discovered that human plasma could be used in blood replacement therapy. During the War, difficulties of supply and storage of whole blood and plasma meant battlefield shock could not be treated as effectively as possible. The need for plasma proteins which could be stored and used on the battlefield led Cohn and others (U.S. Pat. No. 2,390,074 (1945) and the *J. Amer. Chem. Soc.*, 68; p459 (1946)) to discover that proteins present in plasma could be fractionated by selective precipitation in the presence of water-soluble organic solvents or neutral salts. For a review of plasma fractionation see, "The Plasma Proteins", Second Edition, Volume III, pp 548–550, Academic Press, New York, N.Y. (1977). The concentrated protein mixtures could then be introduced into patients as needed. For example, if excess bleeding was the problem, the physician could inject a fibrinogen-enriched fraction. If the patient suffered burns or other traumatic injury where the loss of plasma exceeded that of red blood cells, the physician could use albumin, the colloid-osmotic regulator of plasma.

In Cohn fractionation, ethanol is added to plasma and the pH is lowered at sub-zero temperatures to selectively precipitate protein. After the precipitate is separated from the supernatant, the pH of the supernatant is lowered, and/or more alcohol is added to precipitate another fraction.

Today, this method of fractionation is still being used to separate biologically active proteins that possess certain therapeutic qualities. For instance, Factor VIII or antihemophilic factor is useful against hemophilia; plasminogen, a precursor of plasmin, is used in the treatment of acute thromboembolic disorders; gamma globulins, including immune serum globulin and intravenous gamma globulin, are employed in the treatment of congenital gamma globulin deficiency, measles, poliomyelitis and hepatitis A and B; fibronectin has been identified as active in treatment of burns, shock, cancer, etc.; anti-thrombin III is a coagulation inhibitor; cryoprecipitate itself may be used directly for classic hemophilia; Plasma Protein Fraction and albumin are useful in treatment of shock due to burns, crushing injuries, abdominal emergencies, and any other trauma producing a predominant loss of plasma fluids but not red cells; and α$_1$-proteinase inhibitor can be employed in the treatment of emphysema.

Human α$_1$-antichymotrypsin (ACT) is a serine protease inhibitor that has, until now, only been isolated from human plasma or serum. Although the precise biological function of ACT has not yet been determined, it appears to be a multifunctional protein and its use for various therapies has been suggested. (See, for example, U.S. Pat. No. 5,008,242 to J. Lezdey, et al.)

There is evidence to indicate that an important function of ACT is the inhibition of proteases, such as chymotrypsin-like protease, mast cell chymase, leukocyte cathepsin G (see Beatty, K., Bieth, J., Travis, J.: Kinetic of association of serine proteinases with native and oxidized α$_1$-proteinase inhibitor and α$_1$-antichymotrypsin, *J. Biol. Chem.* 1980; 255:3931–3934) and pancreatic elastase (see Laine, A., Davril, M. Rabaud, M., et al.: Human serum α$_1$-antichymotrypsin is an inhibitor of pancreatic elastases, *Eur. J. Biochem.* 1985; 151:327–331 and Davril, M., Laine, A., Hayem, A.: Studies on the interactions of human pancreatic elastase 2 with human α$_1$-proteinase inhibitor and α$_1$-antichymotrypsin, *Biochem. J.* 1987; 245:699–704).

The biological properties of intact, cleaved and complexed forms of ACT indicate the proteolytic-character of the protein may have a potential role for therapeutic use in regulating infectious disease, pancreatitis, lung disease and skin inflammation (see Rubin, H.: The biology and biochemistry of antichymotrypsin and its potential roles as a therapeutic agent, *Biol. Chem. Hoppe-Sayler* 1992; 373(7):497–502).

J. Travis et al. purified ACT to homogeneity from a human plasma pool (Travis, J., Garner, D., Bowen, J.: Human α$_1$-antichymotrypsin: purification and properties, *Biochemistry* 1978; 17:5647–5651).

T. Katsunuma and his colleagues purified a DNA-binding protein, thought to be a tumor marker, to homogeneity (Katsunuma, T. et al.: Purification of a serum DNA binding protein (64DP) with a molecular weight of 64,000 and its diagnostic significance in malignant diseases, *Biochem. and Biophys. Res. Comm.*, 93(2):552–557 (1980)). Later, the DNA-binding protein was found to be ACT. Katsunuma used human serum as the starting material. They first eluted 64DP from DEAE Sephadex with 225 mM NaCl. After dialysis, the 64DP was further purified on DNA Cellulose. Finally to achieve homogeneity, 64DP was precipitated with ammonium sulfate and separated from contaminating proteins on a size exclusion column.

In addition to isolation from whole plasma, human ACT has been cloned, sequenced and expressed in *Escherichia coli* (see Rubin, H. et al.: Cloning, expression, purification and biological activity of recombinant native and variant human antichymotrypsins, *J. Biol. Chem.* 1990; 265:1199–1207). Rubin et al. used a Sepharose Fast Q column to separate ACT activity from the crude bacterial lysate. The partially purified ACT was then adsorbed to DNA Cellulose and eluted in 350–400 mM KCl.

Because of the potential uses of ACT, there is now a need for more efficient ways of preparing large quantities of ACT from human plasma especially from plasma fractions that also include varying amounts of PI and AT-III.

Unexpectedly, we discovered that ACT can be purified from Cohn Fraction IV-1. Fraction IV-1 contains many different proteins and difficulties in separation preclude most commercial uses of this plasma fraction. Isolation of ACT would therefore be a beneficial use of this otherwise underutilized and normally discarded plasma fraction.

Compared to human serum, Cohn Fraction Paste IV-1 contains higher concentrations of proteins, such as PI and AT-III, that are closely related to ACT and would be expected to co-purify with ACT. During the fractionation process to IV-1 paste, ACT is only concentrated 1–2 fold, while PI is concentrated 3–10 fold and AT-III is concentrated 2–3 fold. The concentrations of the proteins in the IV-1 paste are 30 mg PI/g paste, 5 mg AT-III/g paste and 5–10 mg ACT/g paste. Considering the difficulty in separating ACT from these other proteins and its status as a minor component, it would be considered unlikely that Fraction IV-1 paste would be a suitable source of ACT. Surprisingly, we were able to isolate 2-3 g ACT at a purity ≧90% from approximately 2.9 kg of IV-1 paste using a modified form of the procedure of Katsunuma, et al.

In addition to its demonstrated use an as in vitro serine protease inhibitor (e.g., it can be used as a reagent for PI studies), we have proposed how ACT may be of potential therapeutic use. Details of our discoveries are disclosed below.

SUMMARY OF THE INVENTION

Our method of preparing human alpha$_1$-antichymotrypsin (ACT) from a solution which also includes alpha$_1$-proteinase inhibitor (PI) and antithrombin III (AT-III) comprises the steps of (A) contacting the solution containing ACT with an ion exchange resin at a conductivity (ionic strength) and at pH sufficient to adsorb ACT;

(B) washing the adsorbent using a solution having pH, and conductivity sufficient to remove substantially all PI and AT-III while not removing the adsorbed ACT; and (C) eluting the ACT from the resin.

In one preferred embodiment, step (C) is followed by further purification steps of contacting the eluate solution of step (C) with DNA-cellulose under conditions and pH sufficient to adsorb ACT and then elute the ACT from the DNA cellulose.

In another preferred embodiment, the ACT is prepared from a suspension of Cohn Fraction IV-1 paste which includes an aqueous solution of the ACT, PI and AT-III having a conductivity of 1.0–2.5 mmho/cm and a pH of about 6.45 to 6.55. The ACT is purified using step (A) by chromatography on an anion exchange resin (i.e., DEAE-Sepharose®) at about pH 6.5 followed by washing the DEAE-Sepharose® with a wash solution having a pH of about 6.5 and a conductivity of 7.4 to 7.8 mmho/cm and eluting the ACT at a pH of about 6.5 and a conductivity of 9 to 10.5 mmho/cm and, finally, by adsorption to DNA-cellulose at pH 6.8 prior to final elution of the ACT.

BRIEF DESCRIPTION OF THE FIGURES

FIG. 1 is a generalized flow chart showing how the preferred starting material (Cohn fraction IV-1 paste suspension) is fractionated from human plasma. FIG. 2 is a flow chart showing the preferred steps of our ACT purification process.

MATERIALS AND METHODS

Purified $\alpha_1$-antichymotrypsin, $\alpha_1$-antiproteinase inhibitor and antithrombin III from human plasma, rabbit antibodies to human ACT and human neutrophil cathepsin G were purchased from Athens Research, Athens, Ga. DNA-cellulose (5 ml) was purchased from Pharmacia, Inc. Native calf thymus DNA and cellulose scale-up process DNA-cellulose preparation, succinyl-ala-ala-pro-phe-p-nitroanilide and bovine chymotrypsin were purchased from Sigma Chemical Co., St. Louis, Mo. Cohn Fraction IV-1 was obtained from Miles Inc. DEAE-Sepharose® is a registered trademark of Pharmacia, Inc. for its beaded agarose anion exchange material.

DNA-Cellulose Preparation for Scale-Up Process

DNA-cellulose (3 L) was prepared according to the method of Litman (see Litman, R. M.: A deoxyribonucleic acid polymerase from *Micrococcus lutens* (*Micrococcus hysodeikticus*) isolated on deoxyribonucleic acid-cellulose, *J. Biol. Chem.* 1968; 243:6222–6233). Cellulose (1 kg) was washed for 10 minutes with 1N HCL (15 L), rinsed with water and dried by air. Native calf thymus (16 g) was mixed with cellulose (1 kg) in 8 L of 10 mM NaCL. The lumpy mixture was spread out and dried under a blower for 3–5 hours and finally allowed to stand overnight in the open. The dry matrix was crushed and resuspended in ethanol. The slurry was then irradiated by a UV lamp to form crosslinks to the cellulose.

Purification of Human ACT

Cohn Fraction IV-1 paste prepared generally in accordance with the fractionation method of Cohn et al., *J. Amer. Chem. Soc.* 1948;68:459, including ACT, PI and AT-III, was suspended in 24 volumes of 0.01M Tris pH 9.3 and heated at 40° C. for one to one and a half hours. The fraction IV-1 paste suspension was adjusted to pH 6.5 (70 liters) and was loaded on a 30 kg DEAE-Sepharose® column. The DEAE column was equilibrated with one column volume of 25 mM NaKPO$_4$ pH 6.5 and washed overnight with more than 10 column volumes of 75 mM NaKPO$_4$ pH 6.5, 1 mM EDTA, to give a stable baseline. The partially purified ACT was eluted with 3–5 volumes of 100 mM NaKPO$_4$ pH 6.5. The 100 mM NaKPO$_4$ eluate was ultrafiltered/diafiltered against 0.01M K$_2$HPO$_4$ pH 6.8 (conductivity 1–2 mmho/cm) in a PM-10 3 ft.$^2$ cartridge and batch contacted with the DNA-cellulose (3 L) in the barrel of the DNA column for 90 minutes. The column was washed from the bottom up with 85 mMNaCl in 0.01M K$_2$HPO$_4$, 1 mM EDTA pH 6.8 (conductivity 8–9 mmho/cm) wash buffer overnight. After a stable effluent A$_{280}$ of 0.03 was reached, the column was eluted from the bottom up with 330 mM NaCl in 0.01M K$_2$HPO$_4$, 1 mM EDTA pH 6.8 elution buffer. The eluate was frozen at –70° C. in aliquots.

Enzyme and Inhibitory Activity Assay of ACT

Human neutrophil cathepsin G and bovine chymotrypsin esterolytic activity were measured using succinyl-ala-ala-pro-phe-p-nitroanilide as substrate (see DelMar, E. G., Largman, C., Broderick, J. W., et al.: A sensitive new substrate for chymotrypsin, *Anal. Biochem.* 1979; 99:316–329). A Sequence Information Sheet for the above substrate is included at the end of this application. Inhibitory activity was measured by mixing a fixed quantity of enzyme (cathepsin G/chymotrypsin) with varying amount of ACT. After incubation for 5 minutes at 25° C. the mixtures were assayed for esterolytic activity. An extinction coefficient of 6.2 (1% solution, 280 mM) determined with purified inhibitor was used for the determination of protein concentration (see Babul, J., Stellwagen, E.: Measurement of protein concentration with interferences optics, *Anal. Biochem.* 1969; 28:216–221). Inhibitory specific activity was expressed as the ratio of inhibitory activity per protein concentration.

Antigenic Activity of ACT Determined by RID and ELISA

The antigenic activity of the ACT was determined by a radial immunodiffusion kit from The Binding Site (San Diego, Calif.). The antigenic activity was also determined by enzyme linked immunosorbent assay (ELISA). Purified ACT standard at a concentration range of 0.1–10 ng/ml or purified ACT preparation samples were captured with rabbit antibody to ACT coated plates. A biotinylated rabbit antibody to ACT was added to the plates, following incubation with peroxidase conjugated streptavidin and substrate (tetramethyl benzidine) to detect the activity. Antigenic specific activity was measured as the ratio of antigenic activity per protein concentration.

Antigenic Activity of PI Determined by ELISA

The antigenic activity of PI was determined by enzyme linked immunosorbent assay (ELISA). Goat anti-human $\alpha_1$-antiproteinase inhibitor (Cappel, NC) is used as a coating antibody. Purified PI (Athens Research), purified ACT preparation samples or lyophilized plasma standard of 1.3 mg/mL at a concentration range of 0.78–25 ng/ml were captured with goat anti-human $\alpha_1$-antiproteinase inhibitor coated antibody. Peroxidase conjugated goat anti-human $\alpha_1$-antiproteinase inhibitor was added to the plates, following incubation with substrate (tetramethyl benzidine) to detect the activity. Samples were compared against a standard curve of absorbance vs. antigen concentration.

Enzyme and Inhibitory Activity Assay of AT-III
(Antithrombin III)

This is a two-stage assay in which plasma standard or a concentration of known AT-III activity and samples are diluted in buffer containing heparin and incubated with bovine thrombin (Stage I). Chromogenic substrate S-2238 (H-D-phenylalanyl-L-pipecolyl-L-arginine-P-nitroaniline 2 HCl, Chromogenix AB, Sweden) is then added, and hydrolyzed by any excess thrombin which has not been inhibited by AT-III, released P-nitroanilide and absorbance at 405 nm is quantitated. AT-III concentration is inversely proportional to the degree of hydrolysis (absorbance) by measuring the absorbance at 405 nm.

SDS PAGE and Western Blotting

Analytical electrophoresis was carried out on Tris-glycine 8–16% polyacrylamide gradient slab gels (purchased from Novex System, San Diego, Calif.) using the gel buffer system of Novex containing Tris-glycine, 0.1% SDS pH 8.3. Purified ACT standard and sample preparations were prepared in sample buffer containing Trisglycine, 2% SDS, 10% β-mercaptoethanol for 10 minutes in boiling water. Molecular weight electrophoresis calibration kits from Novex Systems were used for molecular weight determination. Proteins were detected by Coomassie Brilliant Blue G-250. Western blotting was performed from gel to nitrocellulose membrane and detected by rabbit antisera to human ACT and alkali phosphate conjugated goat anti rabbit IgG.

HPLC Analysis

ACT standard from Athens Research and purified ACT from the scale-up process were analyzed on TSK 3000 SW with 0.05M $Na_2HPO_4$, 0.15M NaCl pH 6.5 as the mobile phase.

RESULTS

To prepare human ACT, Cohn Fraction IV-1 paste suspension was employed as starting material. Fraction IV-1 paste contains approximately the following mg/g paste of three proteinase inhibitors: $\alpha_1$-proteinase inhibitor (PI)—30.0; ACT—5–10.0 determined by antigenic activity ELISA and AT-III—5.0 measured by enzyme inhibitory activity. ACT purification by PEG precipitation, S-Sepharose® and Q-Sepharose® chromatography was unfavorable as there was no improvement in purity. Ammonium sulfate fractionation, chelating column and Cibachrome Blue® column for the purification process were unacceptable due to low yield and low purity of ACT.

When employing Fraction IV-1 paste suspension (20733-91-1) in 0.01M Tris pH 6.5 at low conductivity (1.0–2.5 mmho/cm) on DEAE-Sepharose®, more than 91% of total protein was present in the 0.025M $NaKPO_4$ pH 6.5 flow through fraction (20767-36-1 and -2) and 0.075M $NaKPO_4$ pH 6.5 wash fraction (20767-36-3) (Table 1).

TABLE 1

| DEAE-Sepharose Column (10 ml) | | | |
| --- | --- | --- | --- |
| Sample | Total ACT μg | Yield % of Total ACT | Specific Activity mg ACT/ mg Protein |
| FIV-1 Paste Suspension (20733-91-1) | 4,326 | 100 | 0.023 |
| 0.025M $NaKPO_4$ pH 6.5 Flow thru (20767-36-1 & -2) | 257.2 | 6.0 | 0.004 |
| 0.075M $NaKPO_4$ pH 6.5 Wash (20767-36-3) | 166.5 | 3.8 | 0.003 |
| 0.1M $NaKPO_4$ pH 6.5 Eluate (20767-36-4 & -5) | 2,188.3 | 50.6 | 0.169 |
| 0.2M $NaKPO_4$ pH 6.5 Eluate (20767-36-6) | 732 | 16.9 | 0.04 |

More than 50% of ACT eluted at 0.1M $NaKPO_4$ pH 6.5 (20767-36-4 and -5) and there was a seven-fold increase in ACT specific activity. However, loading Fraction IV-1 paste suspension in 0.01M $K_2HPO_4$ pH 6.8 directly onto a DNA-cellulose column (5 ml) gave only 10% recovery yield with a four to ten fold increase in purity after elution with 0.01M $K_2HPO_4$, 0.33M NaCl pH 6.8. Therefore, DEAE-Sepharose® is the preferred first step for ACT prepared from Fraction IV-1 paste suspension.

The following examples were carried out with Cohn Fraction IV-1 paste suspension in 0.01M Tris pH 6.5 at conductivity 1.0–2.5 mmho/cm, followed by DEAE-Sepharose® and DNA-cellulose chromatography.

EXAMPLE 1

ACT in Cohn Fraction IV-1 paste was suspended in 0.01M Tris pH 6.5 and purified through a DEAE-Sepharose® column. The column was washed with 0.025M to 0.075M Sodium Phosphate ($NaHPO_4$) pH 6.5, conductivity=1.9 to 5.3 mmho/cm buffer and 3.6% of the total ACT was eluted with 0.1M Sodium Phosphate pH 6.5 (conductivity: 6.5 mmho/cm) (21864-4-C) and 46% of the total ACT with three and a half fold increase in specific activity (0.072 mg ACT/mg protein) eluted at 0.2M Sodium Phosphate pH 6.5 (conductivity 13.0 mmho/cm) (21864-4-D) (Table 2).

TABLE 2

| Comparison of Elution Buffer System on DEAE-Sepharose Column for ACT Purification | | | |
| --- | --- | --- | --- |
| Sample | Total ACT μg | Yield % | Specific Activity mg ACT/mg Protein |
| A. | | | |
| FIV-1 Paste suspension | 10,250 | 100 | 0.021 |
| 0.025M $NaHPO_4$ pH 6.5 Flow | 1,147 | 11.2 | 0.007 |

TABLE 2-continued

Comparison of Elution Buffer System on
DEAE-Sepharose Column for ACT Purification

| Sample | Total ACT µg | Yield % | Specific Activity mg ACT/mg Protein |
|---|---|---|---|
| Thru (21864-4-A) | | | |
| 0.075M NaHPO$_4$ pH 6.5 Wash (21864-4-B) | 335 | 3.3 | 0.003 |
| 0.1M NaHPO$_4$ pH 6.5 Eluate (21864-4-C) | 372 | 3.6 | 0.009 |
| 0.2M NaHPO$_4$ pH 6.5 Eluate (21864-4-D) | 4,760 | 46.4 | 0.072 |
| B. | | | |
| FIV-1 Paste Suspension DP 1279 | 4,580 | 100 | 0.024 |
| 0.025M NaKPO$_4$ pH 6.5 Flow Thru (21893-17A) | 457.6 | 10.0 | 0.009 |
| 0.075M NaKPO$_4$ pH 6.5 Wash (21893-17B) | 1,200.5 | 26.2 | 0.013 |
| 0.1M NaKPO$_4$ pH 6.5 Eluate (21893-17C) | 2,059.6 | 45.0 | 0.134 |
| 0.2M NaKPO$_4$ pH 6.5 Eluate (21893-17D) | 235.6 | 5.1 | 0.03 |

However, with 0.025M to 0.075M Sodium Potassium Phosphate (NaKPO$_4$) pH 6.5, conductivity: 2.8 to 7.4 mmho/cm buffer wash, partially purified ACT eluted at 0.1M NaKPO$_4$ pH 6.5 (conductivity: 9–10 mmho/cm) (21893-17-C) from DEAE-Sepharose® and gave 45% yield with 5.6 fold increase in specific activity (0.134 mg ACT/mg protein) (Table 2). The results in Table 2 indicate that employing the equilibrated buffer system 0.025M NaKPO$_4$ pH 6.5 (conductivity: 2.8–3.0 mmho/cm) for DEAE-Sepharose® and loading Cohn Fraction IV-1 paste suspension (conductivity: 1.0–2.5 mmho/cm) on DEAE-Sepharose® column, remove unwanted protein by washing with 0.075M NaKPO$_4$ pH 6.5 (conductivity: 7.0–7.8 mmho/cm) and partially purified ACT (DEAE-eluate) elutes with 0.1M NaKPO$_4$ pH 6.5 (conductivity: 10 mmho/cm) for further purification through a DNA-cellulose column.

EXAMPLE 2

When Cohn Fraction IV-1 paste suspension (DP 1279) with low antigenic specific activity (0.024 mg ACT/mg protein) was used as starting material for purification through DNA-cellulose (Pharmacia), there was a low yield of ACT (17%), low purity (antigenic specific activity 0.12–0.32 mg ACT/mg protein) and low ACT binding capacity (0.1–0.2 mg ACT/mL DNA-gel, Table 3).

TABLE 3

FIV-1 Paste Suspension on DNA-Cellulose Column (5 ml)

| Sample | Total ACT µg | Yield % of Total ACT | Spec. Activity mg ACT/mg Protein |
|---|---|---|---|
| FIV-1 Paste Suspension (DP1279) (21893-20-1) | 4,580 | 100 | 0.024 |
| Flow Thru (21893-20-A) | 1,775.2 | 38.8 | 0.012 |
| 0.085M NaCl Wash (21893-20-B) | 356 | 7.8 | 0.017 |
| 0.33M NaCl Eluate (21893-20-33,34,35) | 765.6 | 16.7 | 0.324 |

However, partially purified ACT in DEAE-eluate (20767-93-1, 21893-15-1) with higher antigenic specific activity (0.16–0.25 mg ACT/mg protein) as starting material resulted in higher yield (61.2–67.1%), higher purity (antigenic specific activity 1.07–1.47 mg ACT/mg protein) and higher ACT binding capacity (0.6–1.2 mg ACT/mL DNA-gel, Table 4). Based on these data, DNA-cellulose is the second step for purified ACT prepared from partially purified DEAE-eluate.

TABLE 4

DEAE Eluate on DNA-Cellulose Column

| Sample | Total ACT Antigenic µg | Yield % | Specific Activity mg ACT/mg Protein |
|---|---|---|---|
| EXPERIMENT 1 | | | |
| Conc. of DEAE-Eluate (20767-93-1) | 1,605.5 | 100 | 0.248 |
| Flow Thru (20767-93-A) | 30.6 | 1.9 | 0.004 |
| 0.085M NaCl Wash (20767-93-B) | 38.3 | 2.4 | 0.07 |
| 0.33M NaCl Eluate (20767-93-C&D) | 982 | 61.2 | 1.07 |
| EXPERIMENT 2 | | | |
| Conc. of DEAE-Eluate (21893-15-1) | 4,230 | 100 | 0.164 |
| Flow thru (21882-29-A) | 51.4 | 1.2 | 0.003 |
| 0.085 NaCl Wash (21882-29-B) | 29.4 | 0.7 | 0.03 |
| 0.33M NaCl Eluate (21882-29-21,22,23) | 2,837.2 | 67.1 | 1.47 |

EXAMPLE 3

Our overall preferred process for preparing ACT from plasma is shown in FIG. 2. In a proposed scale-up process, 2 lots of partially purified ACT prepared from Fraction IV-1 paste suspension (70 kg) at pH 6.5, conductivity 1.0–2.0 mmho/cm, through DEAE-Sepharose® column (30 L) resulted in a 17–34% yield at 0.1M NaKPO$_4$ pH 6.5 eluate (conductivity 9.5–10.5 mmho/cm) with antigenic specific activity increased from 0.022 to 0.108–0.194 mg ACT/mg protein and a four to nine fold increase in purity (Table 5).

TABLE 5

Prepare Purified ACT by Scale-up Process

| Sample | Total ACT Antigenic mg | Yield % | Antigenic Specific Activity mg ACT/mg Protein |
|---|---|---|---|
| EXPERIMENT 1 | | | |
| Step 1: DEAE-Sepharose (30 L) | | | |
| FIV-1 Paste Suspension (21893-58-2) | 25,690 | 100 | 0.022 |
| DEAE Flow Thru (21893-58-3) | 885 | 3.4 | 0.003 |
| DEAE Wash (21893-58-4) | 4,865 | 18.9 | 0.015 |
| DEAE Eluate (21893-58-5) | 8,710 | 33.9 | 0.194 |
| Step 2: DNA-Cellulose (3 L) | | | |
| DF/UF Conc DEAE-Eluate (21893-58-6) | 8,494 | 33.1 | 0.187 |
| DNA-Eluate (21869-35) | 3,464 | 13.5 | 1.24 |
| EXPERIMENT 2 | | | |
| Step 1: DEAE-Sepharose | | | |

TABLE 5-continued

Prepare Purified ACT by Scale-up Process

| Sample | Total ACT Antigenic mg | Yield % | Antigenic Specific Activity mg ACT/mg Protein |
|---|---|---|---|
| (30 L) | | | |
| FIV-1 Paste Suspension (21882-65-1) | 31,150 | 100 | 0.025 |
| DEAE-Flow Thru (21882-65-2) | 1,854 | 6.0 | 0.008 |
| DEAE-Wash (21882-65-3) | 6,470 | 20.8 | 0.008 |
| DEAE-Eluate (21882-65-4) | 5,265 | 16.9 | 0.108 |
| Step 2: DNA-Cellulose (3 L) | | | |
| DF/UF Conc. DEAE-Eluate (21882-65-5) | 4,939 | 15.9 | 0.094 |
| DNA-Eluate (21869-37) | 2,142 | 6.9 | 1.24 |

Insignificant loss of activity of ACT was obtained through the DF/UF step. DEAE-eluate was further purified through DNA-cellulose column (3 L) and gave overall yield of 6.9–13.5% with antigenic specific activity increased from 0.108–0.194 to 1.24 mg ACT/mg protein. Two lots of DNA-eluate (21869-35, 21869-37) were further diafiltered and ultrafiltered, formulated in PBS buffer pH 7.0 at 10–20 mg/mL (21893-61-3 and 21882-68) and stored at −70° C. for further in vitro and in vivo studies.

Characterization of Purified ACT

A. Antigenic and Inhibitory Activity

Purified ACT (21893-61-3, 21882-68) prepared from Cohn Fraction IV-1 by scale-up process including the in-house DNA-cellulose column resulted in specific activity of >1 mg/mg total protein of inhibitory activity to both human cathepsin G and to bovine chymotrypsin when compared to purified ACT standard (freeze dried form) purchased from Athens Research, Atlanta, Ga. (Table 6).

B. SDS PAGE and HPLC Analysis

When 5 μg, 10 μg, 20 μg per lane was applied on 6–18% SDS-PAGE under reducing conditions, ACT standard prepared from plasma and purified ACT (21893-61-3) prepared from Fraction IV-1 paste had similar molecular weight ranges (59.2–61.9 kD) and similar purity (≧90%). By Western blotting, ACT prepared from plasma and Fraction IV-1 paste could be detected with anti-human ACT antibody, but there were no significant bands detected in either preparations with either anti-$\alpha_1$-PI or anti-AT-III antibody. Purified ACT (21893-61-3) contained trace amount of degraded fragment (25.5 kD) which bound to anti-human ACT antibody in Western blotting. HPLC analysis showed that purified ACT from both plasma and Fraction IV-1 paste had similar retention times and more than 90% purity.

C. IEF

ACT standard from Athens Research and purified ACT from Fraction IV-1 paste (21893-61-3, 21882-68) were analyzed on Novex IEF (pH 3–10, Novex System, San Diego, Calif.). Both ACT from plasma (see Laursen, I. and Lykkesfeldt, A. E.: Purification and characterization of an $\alpha_1$-antichymotrypsin-like 66 kD protein from the human breast cancer cell line, MCF-7, *Biochem. Biophys. Acta.* 1992; 1121:119–129) and from Fraction IV-1 paste had similar pI's of around 3.8–4.3 compared with pI's of around 4.6–5.1 for AT-III and 4–5 for PI.

D. Specifications of Purified ACT (21882-68)

2.4 g of purified ACT (21882-68), 10 mg/ml in PBS buffer prepared from two runs of the scale-up process has been characterized. The purified ACT has ≧90% purity by IEF, SDS PAGE and HPLC, biological activity comparable to ACT standard (purchased from Athens Research) and contains 0.7 endotoxin units per mg $A_{280}$ protein by LAL assay (Table 7).

TABLE 7

Characteristics of Purified ACT (21882-68)

| Volume Characteristics | 259 mL, 50 vials (5 mL/vial) |
|---|---|
| Appearance (Visual) | Clear, colorless solution |
| Protein Conc. ($A_{280}$) 0.1% E1cm = 0.62 | 10.1 ± 0.4 mg/mL |
| PBS Buffer pH | 7.1 ± 0.1 |
| Identification | |
| Isoelectric Focusing | IEF spectrotype about 90% complies with ACT std.* |

TABLE 6

Antigenic and Inhibitory Activities of Purified ACT

| | | ACT Activity (mg/mL) | | | Spec. Act. mg ACT/mg Protein | | |
|---|---|---|---|---|---|---|---|
| | Protein | | Inhibitory | | | Inhibitory | |
| Purified ACT | Conc (mg/mL) | Antigenic | Cathepsin G | Chymotrypsin | Antigenic | Cathepsin G | Chymotrypsin |
| 21893-61-3 | 21.7 | 26.2 | 24.3 | — | 1.2 | 1.1 | — |
| 21882-68 | 9.7 | 9.6 | 12.1 | 14.1 | 0.99 | 1.36 | 1.45 |
| ACT Standard (Athens Research) | 2.63 | 2.53 | 2.9 | 2.8 | 0.96 | 1.1 | 1.05 |

TABLE 7-continued

Characteristics of Purified ACT (21882-68)

| Purity | |
|---|---|
| SDS PAGE (6–18%) - Reduced | ≧90% ACT std. with trace amount of degraded fragment (25.5 kD) |
| HPLC | Area % of ACT std. ≧90% |

TABLE 7-continued

Characteristics of Purified ACT (21882-68)

| | |
|---|---|
| Endotoxin (LAL) | 0.7 EU per mg $A_{280}$ protein |
| Biological activity (antigenic, inhibitory to human cathepsin G and bovine chymotrypsin | Comparable to ACT std. |

*Purchased from Athens Research

DISCUSSION

Cohn Fraction IV-1 paste contains a slightly higher concentration of ACT (5–10 mg/g paste) than plasma (4–5 mg/g protein). Therefore, Cohn Fraction IV-1 paste suspension fractionated from human plasma is the preferred starting material for further purification. Human ACT has been purified to homogeneity from human plasma pool by various procedures, such as ammonium sulfate fractionation, Cibacron Blue® chromatography, SP-Sephadex® or QAE-Sephadex®, DNA-cellulose, and S-300 chromatography. However, contrary to the published results of others, we found that ACT purification with ammonium sulfate fractionation or direct DNA-cellulose chromatography resulted in low yield and low purity when employing Fraction IV-1 paste as starting material.

Prolastin®, a commercially available plasma-derived PI preparation (Miles Inc.) purified by PEG precipitation and DEAE-Sepharose® from Fraction IV-1 paste suspension, is comprised of 600 µg PI per mg protein and a small amount of ACT, 29 µg per mg protein. This reinforces our findings that PEG precipitation of Fraction IV-1 paste results in low yield and low purity of ACT. Another commercial plasma protein preparation is antithrombin III (Thrombate®, Miles Inc.) prepared from Fraction IV-1 paste suspension by heparin-agarose chromatography. Our studies showed that more than 91% of ACT did not bind to the heparin-agarose column. This would imply that ACT has the potential to be prepared as an AT-III side product.

Cohn Fraction IV-1 paste contains three major proteinase inhibitors; PI (30 mg/g paste), AT-III (5 mg/g paste) and ACT (5–10 mg/g paste). These proteins have very similar pI values; 4.6–5.1 for AT-III, 4–5 for PI, 3.8–4.3 for ACT; and similar molecular weights: 58 kD for AT-III, 53 kD for native PI, and 58–68 kD for native ACT. Optimal separation of ACT from PI and AT-III from Cohn Fraction IV-1 paste was dependent on employing the right kind of anion exchange resin with the right kind of buffer, pH and ionic strength (conductivity) to remove PI and AT-III in the purified ACT preparation. ACT purification from Cohn Fraction IV-1 paste suspension at pH 6.5 and conductivity of 1–2.5 mmho/cm through DEAE-Sepharose® (but not Q-Sepharose®), pre-equilibrated with 0.025M $NaKPO_4$ pH 6.5 buffer (conductivity 2.5–3 mmho/cm), removed most PI at 0.075M $NaKPO_4$ pH 6.5 (conductivity 7.4–7.8 mmho/cm) and ACT was eluted at 0.1M $NaKPO_4$ pH 6.5, 9–10.5 mmho/cm conductivity. The partially purified ACT from DEAE-eluate containing AT-III and traces of PI was further purified through DNA-cellulose. Most of the AT-III and traces of the PI did not bind to DNA-cellulose when the column was washed with 0.01M $K_2HPO_4$ buffer, 0.085M NaCl pH 8.0 conductivity 8–9 mmho/cm, and only activated ACT specifically absorbed to DNA-cellulose and eluted at 0.33M NaCl in 0.01M $K_2HPO_4$ pH 6.8 (conductivity 24–25 mmho/cm).

Overall yield and purity of ACT following the DNA-cellulose column are dependent upon purity of the ACT solution loaded onto the column. DNA-cellulose removed unbound AT-III and PI when partially purified ACT (DEAE-eluate) but not Cohn Fraction IV-1 paste suspension was loaded onto the column. This resulted in highly purified ACT with specific activity of >1 mg/mg protein of inhibitory activity to both human cathepsin G and to bovine chymotrypsin.

Purified ACT prepared from Cohn Fraction IV-1 paste exhibits a similar molecular weight range by SDS PAGE and HPLC analysis and similar isoelectric points when compared with ACT standard prepared from human plasma. The antigenically intact and active ACT can be purified from Cohn Fraction IV-1 paste and further studies of its in vivo biological activity are required to support its therapeutic use.

Given the above examples, it is thought variations will occur to those skilled in the art. Accordingly, it is intended that the invention disclosed here should be limited only by the following claims.

We claim:

1. A method of preparing human alpha-1-antichymotrypsin (ACT) from Cohn Fraction IV-1 paste which includes human ACT and human alpha$_1$ proteinase inhibitor (PI) and human anti-thrombin III (AT-III) comprising the steps of (A) obtaining an aqueous solution of a Cohn Fraction IV-1 paste that includes ACT, PI and AT-III;

(B) contacting the solution with an anion exchange resin at a conductivity of about 1.0 to 2.5 mmho/cm and a pH of about 6.5 to adsorb the ACT, PI and AT-III;

(C) washing the resin under conditions of pH of about 6.5 and conductivity of 7.0 to 7.8 mmho/cm to elute substantially all of the PI and AT-III;

(D) eluting ACT from the resin to form an eluate solution;

(E) contacting the eluate solution at a pH of about 6.8 and a conductivity of 1.0 to 2.0 mmho/cm with DNA-cellulose to adsorb the ACT; and (F) eluting the ACT from the DNA-cellulose.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 4
        ( B ) TYPE: amino acid
        ( C ) STRANDEDNESS: single strand
        ( D ) TOPOLOGY: linear ( i i ) MOLECULE TYPE:
        ( A ) DESCRIPTION: peptide ( i x ) FEATURE:
        ( A ) NAME/KEY: Modified peptide used for enzyme activity assay
        ( D ) OTHER INFORMATION: Peptide is modified with n-terminal
                succinyl group and c-terminal p-nitroanilide group ( x ) PUBLICATION INFORMATION:

(A) AUTHORS: Del Mar, E. G.
            Largman, C.
            Broderick, J. W.
        (B) TITLE: A Sensitive New Substrate for Chymotrypsin
        (C) JOURNAL: Analytical Biochemistry
        (D) VOLUME: 99
        (F) PAGES: 316-329
        (G) DATE: 01-NOV-1979
        (K) RELEVANT RESIDUES IN SEQ ID NO:1: FROM 1 TO 4

(xi) SEQUENCE DESCRIPTION: SEQ ID NO:1:

Ala Ala Pro Phe
 1